US00PP14038P29

(12) United States Plant Patent
Heims

(10) Patent No.: US PP14,038 P2
(45) Date of Patent: Jul. 29, 2003

(54) *SCABIOSA CAUCASICA* PLANT NAMED 'ULTRA VIOLET'

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 10/213,892

(22) Filed: Aug. 6, 2002

(51) Int. Cl.[7] ..... A01H 5/00
(52) U.S. Cl. ..... Plt./263
(58) Field of Search ..... Plt./263

(56) References Cited

U.S. PATENT DOCUMENTS

PP13,446 P2 * 12/2002 Tristram ..... Plt./263

OTHER PUBLICATIONS http://seattlepi.nwsource.com/nwgardens/104325_wingate16.shtml.*

* cited by examiner

*Primary Examiner*—Bruce R. Campell
*Assistant Examiner*—W C Haas
(74) *Attorney, Agent, or Firm*—Klarquist Sparkman, LLP

(57) ABSTRACT

A new and distinct cultivar of *Scabiosa caucasica* plant characterized by its vibrant, deep purple blue flower color.

1 Drawing Sheet

BOTANICAL CLASSIFICATION:
*Scabiosa caucasica.*

The present invention relates to a new and distinct cultivar of *Scabiosa caucasica* and given the cultivar name 'Ultra Violet'. Scabiosa is in the family Dipsacaceae. This new cultivar originated as a select seedling found by Dan Heims in a mass planting of *Scabiosa caucasica* 'Blue Pacific' (unpatented) seedlings.

This new *Scabiosa caucasica* cultivar is distinguished by:

1. Intense, deep purple flowers, darker than any known *Scabiosa caucasica* on the market.
2. Good flower size.
3. Good vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
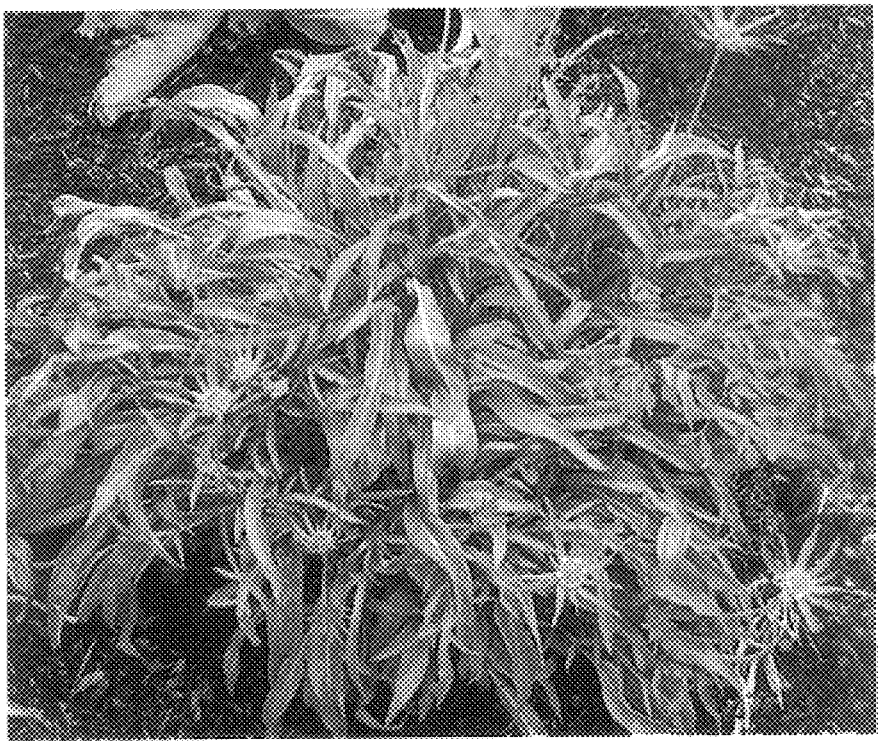
FIG. 1 shows *Scabiosa caucasica* 'Ultra Violet' growing in the ground in the spring before flowering in Canby, Oreg.
Figure 2:
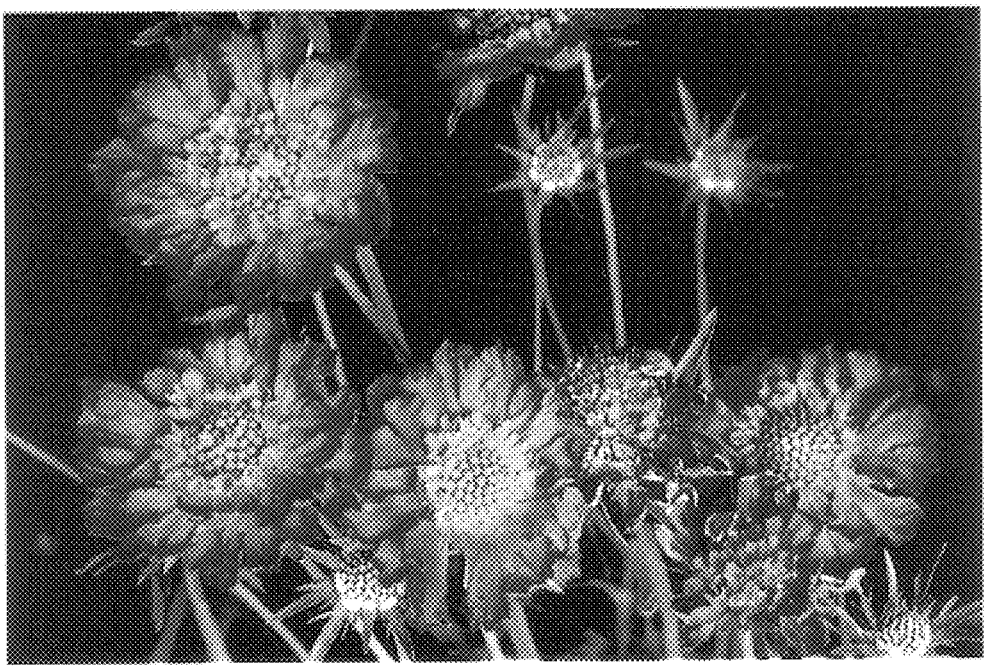
FIG 2 shows the flowers of this new cultivar.

The following is a detailed description of the new *Scabiosa caucasica* cultivar based on observations of a one-year-old specimen grown in a 2-gallon pot in Canby, Oreg. The color descriptions are all based on The Royal Horticultural Society Colour Chart.

Botanical name: *Scabiosa caucasica.*
Cultivar name: 'Ultra Violet'.

Plant:
- *Type.*—Herbaceous perennial.
- *Hardiness.*—USDA Zones 4 to 9.
- *Size.*—33 cm wide and 17 cm. tall.
- *Form.*—Basal clump.

Leaf:
- *Type.*—Simple.
- *Shape.*—Lanceolate.
- *Arrangement.*—Rosette.
- *Blade length.*—8 to 12 cm.
- *Width.*—1.2 to 1.9 cm. at the widest part.
- *Margins.*—Entire.
- *Apex.*—Acuminate.
- *Base.*—Attenuate, continuing down petiole.
- *Texture.*—Glabrous, leathery.
- *Vestiture.*—Ciliate on margins and main vein.
- *Venation.*—Pinnate.
- *Color.*—Topside — Closest to Green 138A. Bottom — Green 138A.
- *Petiole length.*—6 to 8 cm, clasping at the base.
- *Petiole vestiture.*—Glabrous.
- *Petiole color.*—Yellow Green 145C.

Inflorescence:
- *Type.*—Long stalked terminal heads.
- *Peduncle.*—Height: 38 cm. Diameter: 0.2 cm. Vestiture: Puberulous. Color: Yellow Green 146B with Grayed Purple 183A where exposed to sun.
- *Cauline leaves.*—Arrangement: Alternate, clasping, sessile. Shape: Lanceolate, pinnatifid. Size: 13 cm long and 1.9 cm wide. Color: Same as basal leaves.

Flower bud:
- *Size.*—0.2 to 0.4 cm wide and 0.4 to 0.7 cm deep.
- *Shape.*—Ovoid.
- *Color.*—Very light violet, Violet Blue 91D.
- *Vestiture.*—Tomentose.

Flower:
- *Type.*—Perfect, zygomorphic, in hemispherical heads subtended by 2 series of involucral bracts.
- *Size.*—5.5 to 7 cm. wide and 1.8 to 2 cm deep.
- *Ray-like flowers.*—Fan shaped, with 3 large lobe and 2 small lobes. Large lobes are triangular and widest at the top, fringed and sometimes notched, 3.5 cm wide and 2.2 cm deep. Small lobes are 0.5 cm deep and 0.3 cm wide. Tube is 0.4 cm long.

*Disc-like flowers.*—Variable, 1 to 1.5 cm deep and 0.6 to 1.1 cm wide, with lobes unequal.

*Texture.*—Satiny, soft.

*Vestiture.*—Glabrous on top and tomentose on bottom.

*Color.*—Ray, topside — Deep royal purple, closest to Violet Blue 89A but a deeper and more intense. Ray, bottom side — Violet Blue 93A at petal edges to 93B and C in middle and lightening to 91D in tube. Disc, inside — Violet Blue 93A at petal edges to 91C at tube. Disc, outside — Violet Blue 91A at petal edges to 91C at tube.

*Bract* (*at the base of each head*).—Involucral bracts in one to two leafy series, lobes lanceolate in shape.

*Bract size.*—3.5 to 5 cm wide.

*Bract color.*—Yellow Green 146A.

*Calyx.*—Bristly, of 5 setae, twice as long as the scarious involucel, persistent.

*Involucel.*—Persistent at the base of each flower, scarious, white, campanulate, 0.5 cm deep and 0.3 cm wide.

*Pistil.*—1 cm. long, style color is Violet Group 86A.

*Stamen number.*—4.

*Pollen color.*—White 155D.

*Bloom period.*—June through September in Canby, Oreg.

*Fragrance.*—Slight.

Seed:

*Type.*—Achene.

*Size.*—1 cm including persistent involucel.

*Color.*—Gray Brown 199B.

*Fertility.*—Low.

Disease: None observed on plant grown under commercial conditions in Canby, Oreg.

COMPARISONS TO SIMILAR SCABIOSA

Compared to *Scabiosa caucasica* 'Blue Pacific', an unpatented seed variety with darker flowers than the species, the flowers of this new cultivar are much deeper purple blue in color.

I claim:

1. A new and distinct cultivar of *Scabiosa caucasica* plant substantially as shown and described.

* * * * *